United States Patent
Perez et al.

(10) Patent No.: US 11,452,506 B2
(45) Date of Patent: Sep. 27, 2022

(54) PATIENT INTERFACE MODULE (PIM) POWERED WITH WIRELESS CHARGING SYSTEM AND COMMUNICATING WITH SENSING DEVICE AND PROCESSING SYSTEM

(71) Applicant: KONINKLIJKE PHILIPS N.V., Eindhoven (NL)

(72) Inventors: Cesar Perez, Roseville, CA (US); Samuel Sidney Rhodes, Roseville, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 58 days.

(21) Appl. No.: 16/756,314

(22) PCT Filed: Oct. 11, 2018

(86) PCT No.: PCT/EP2018/077764
§ 371 (c)(1),
(2) Date: Apr. 15, 2020

(87) PCT Pub. No.: WO2019/076731
PCT Pub. Date: Apr. 25, 2019

(65) Prior Publication Data
US 2020/0315591 A1    Oct. 8, 2020

Related U.S. Application Data

(60) Provisional application No. 62/574,655, filed on Oct. 19, 2017.

(51) Int. Cl.
*A61B 8/00* (2006.01)
*A61B 8/08* (2006.01)
*A61B 8/12* (2006.01)

(52) U.S. Cl.
CPC .............. *A61B 8/56* (2013.01); *A61B 8/0891* (2013.01); *A61B 8/445* (2013.01); *A61B 8/4472* (2013.01);
(Continued)

(58) Field of Classification Search
CPC ............ A61B 8/12; A61B 8/54; A61B 8/4472; A61B 8/56; A61B 8/445
See application file for complete search history.

(56) References Cited

U.S. PATENT DOCUMENTS 8,364,241 B2 * 1/2013 Hannon ............... A61B 6/4494
600/407
9,649,251 B2 * 5/2017 Fossan ................. A61H 31/004
(Continued)

FOREIGN PATENT DOCUMENTS

EP           2026205 B1 *  1/2011  ......... G06F 9/44505
WO  WO-2012138874 A2 * 10/2012  ............. A61B 5/333
(Continued)

OTHER PUBLICATIONS

International Search Report & Written Opinion of PCT/EP2018/077764, dated Dec. 19, 2018.

*Primary Examiner* — Oommen Jacob
*Assistant Examiner* — Nyrobi Celestine

(57) ABSTRACT

Systems, devices, and methods for intraluminal ultrasound imaging are provided. An intraluminal ultrasound imaging system may include a patient interface module (PIM) in communication with an intraluminal device comprising an ultrasound imaging component and positioned within a body lumen of a patient. The PIM may receive ultrasound echo signals from the intraluminal device, transmit the ultrasound echo signals along a differential signal path, and digitize the ultrasound echo signals. The PIM may transmit the ultrasound wirelessly to a processing system. The PIM may be powered with a wireless charging system, such as an inductive charging system.

20 Claims, 7 Drawing Sheets

(52) U.S. Cl.
CPC ............... *A61B 8/461* (2013.01); *A61B 8/54* (2013.01); *A61B 8/12* (2013.01)

(56) References Cited

U.S. PATENT DOCUMENTS

| | | | |
|---|---|---|---|
| 10,420,507 B2* | 9/2019 | Calcano | G01L 5/0052 |
| 2004/0171970 A1* | 9/2004 | Schleuniger | A61N 1/32 601/2 |
| 2013/0109973 A1* | 5/2013 | Kurokawa | H02J 7/02 600/459 |
| 2013/0303919 A1 | 11/2013 | Corl | |
| 2014/0187963 A1 | 7/2014 | Corl | |
| 2014/0257102 A1 | 9/2014 | Hossack | |
| 2015/0347744 A1* | 12/2015 | Kennedy | A61B 1/00059 600/467 |
| 2018/0161002 A1* | 6/2018 | Alford | A61N 7/02 |
| 2019/0099156 A1* | 4/2019 | Bocca | A61B 5/6898 |
| 2019/0117191 A1 | 4/2019 | Hoffman | |
| 2020/0015779 A1* | 1/2020 | Corl | A61B 5/0066 |

FOREIGN PATENT DOCUMENTS

| | | |
|---|---|---|
| WO | 2016018867 A1 | 2/2016 |
| WO | 2018087050 A1 | 5/2018 |
| WO | 2019076968 A1 | 4/2019 |

\* cited by examiner

PATIENT INTERFACE MODULE (PIM) POWERED WITH WIRELESS CHARGING SYSTEM AND COMMUNICATING WITH SENSING DEVICE AND PROCESSING SYSTEM

CROSS-REFERENCE TO PRIOR APPLICATIONS

This application is the U.S. National Phase application under 35 U.S.C. § 371 of International Application No. PCT/EP2018/077764, filed on Oct. 11, 2018, which claims the benefit of U.S. Provisional Patent Application No. 62/574,655, filed on Oct. 19, 2017. These applications are hereby incorporated by reference herein.

TECHNICAL FIELD

The present disclosure relates generally to intraluminal imaging and, in particular, to receiving and converting imaging signals with a patient interface module (PIM). The PIM may be powered with a wireless power system. The PIM may be configured to communicate signals wirelessly to a processing system.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy with frequencies higher than 2 MHz to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

IVUS catheters may include rotational devices. For a typical rotational IVUS catheter, an ultrasound transducer element is located at the tip of a flexible driveshaft that spins inside a plastic sheath inserted into the vessel of interest. The transducer element is oriented such that the ultrasound beam propagates into the tissue and back. The transducer then listens for the returning echoes reflected from various tissue structures. The returning echoes are generally transmitted to an IVUS processing system along a single analog channel. These transmissions may be prone to electrical noise and electromagnetic coupled interference that may degrade the quality of IVUS images associated with the transmissions. Furthermore, existing IVUS systems typically require an expensive and complex custom cable to transmit signals between the ultrasound transducer element and the processing system. Additionally, existing IVUS systems are typically powered by large cables which reduce their portability. Since the power requirements are high for many of these systems, they also require isolation components to protect patients. Thus, needs exist for improvements in IVUS imaging systems.

SUMMARY

Systems, devices, and methods for intraluminal ultrasound imaging are provided. An intraluminal ultrasound imaging system may include a patient interface module (PIM) in communication with an intraluminal device positioned within a body lumen of a patient. The PIM may receive ultrasound echo signals, transmit the ultrasound echo signals along a differential signal path, and digitize the ultrasound echo signals. The ultrasound echo signals may be transmitted wirelessly to a processing system. The PIM may be powered by a wireless charging system such as an inductive charging system.

Embodiments of the present disclosure provide an intraluminal ultrasound imaging system that may include: a patient interface module (PIM) communicatively disposed between a processing system and an intraluminal ultrasound device configured to be positioned within a body lumen of a patient, the PIM comprising a transmitter, an analog to digital converter (ADC), a communication device, wherein the PIM is configured to be powered by a wireless charging system, wherein the PIM is configured to: transmit, with the transmitter, a first signal to the intraluminal ultrasound device; receive an ultrasound echo signal associated with the first signal from the intraluminal ultrasound device; digitize the ultrasound echo signal with the ADC; and transmit the ultrasound echo signal to the processing system wirelessly via the communication device.

In some embodiments, the processing system is configured to generate an intraluminal ultrasound image representative of the ultrasound echo signal and to display the intraluminal ultrasound image on a display device in communication with the processing system. The wireless charging system may include a rechargeable battery disposed within the PIM and a Qi inductive charging base. The PIM may not transmit or receive signals when connected to the Qi inductive charging base. The PIM may include a switch that prevents receiving or sending signals with the PIM is connected to the Qi inductive charging base. The PIM may be further configured to be powered by a charging cable.

In some embodiments, the PIM further comprises a controller in communication with the transmitter, the ADC, and the communication device. The controller may be a field-programmable gate array (FPGA). The intraluminal ultrasound device may include: a rotatable, flexible elongate drive cable comprising a proximal portion and a distal portion; and an ultrasound element disposed at the distal portion of the drive cable and configured to obtain imaging data of the body lumen while rotating. The intraluminal ultrasound device may be an intravascular ultrasound (IVUS) device configured to be positioned within a blood vessel. The ultrasound echo signal may travel on a differential signal path to the ADC within the PIM. The differential signal path may include one or more amplifiers and bandpass filters.

A method of intraluminal ultrasound imaging is also provided, including: powering, with a wireless charging system, a patient interface module (PIM) communicatively disposed between an intraluminal ultrasound device and a processing system the PIM; controlling, using a transmitter of the PIM, the intraluminal ultrasound device to transmit a first signal while the intraluminal device is positioned within a body lumen of a patient; receiving, with PIM, an ultrasound echo signal associated with the first signal from the intraluminal ultrasound device; digitizing the ultrasound echo signal with an ADC in the PIM; and transmitting the digitized ultrasound echo signal to the processing system via a wireless communication device.

The method may also include displaying, with a display device in communication with the processing system, an intraluminal ultrasound image representative of the ultrasound echo signal. The method may include formatting, by the PIM, the ultrasound echo signal according to an image display format of the display device. The wireless charging system may include a rechargeable battery disposed within the PIM and a Qi inductive charging base. The method may include preventing the transmission of signals by the PIM when the PIM is connected to the Qi inductive charging base. The method may include transmitting the ultrasound echo signals along a differential signal path to the ADC within the PIM.

In some embodiments, the intraluminal ultrasound device includes: a rotatable, flexible elongate drive cable comprising a proximal portion and a distal portion; and an ultrasound element disposed at the distal portion of the drive cable and configured to obtain imaging data of the body lumen while rotating. The intraluminal ultrasound device may be an intravascular ultrasound (IVUS) device configured to be positioned within a blood vessel.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
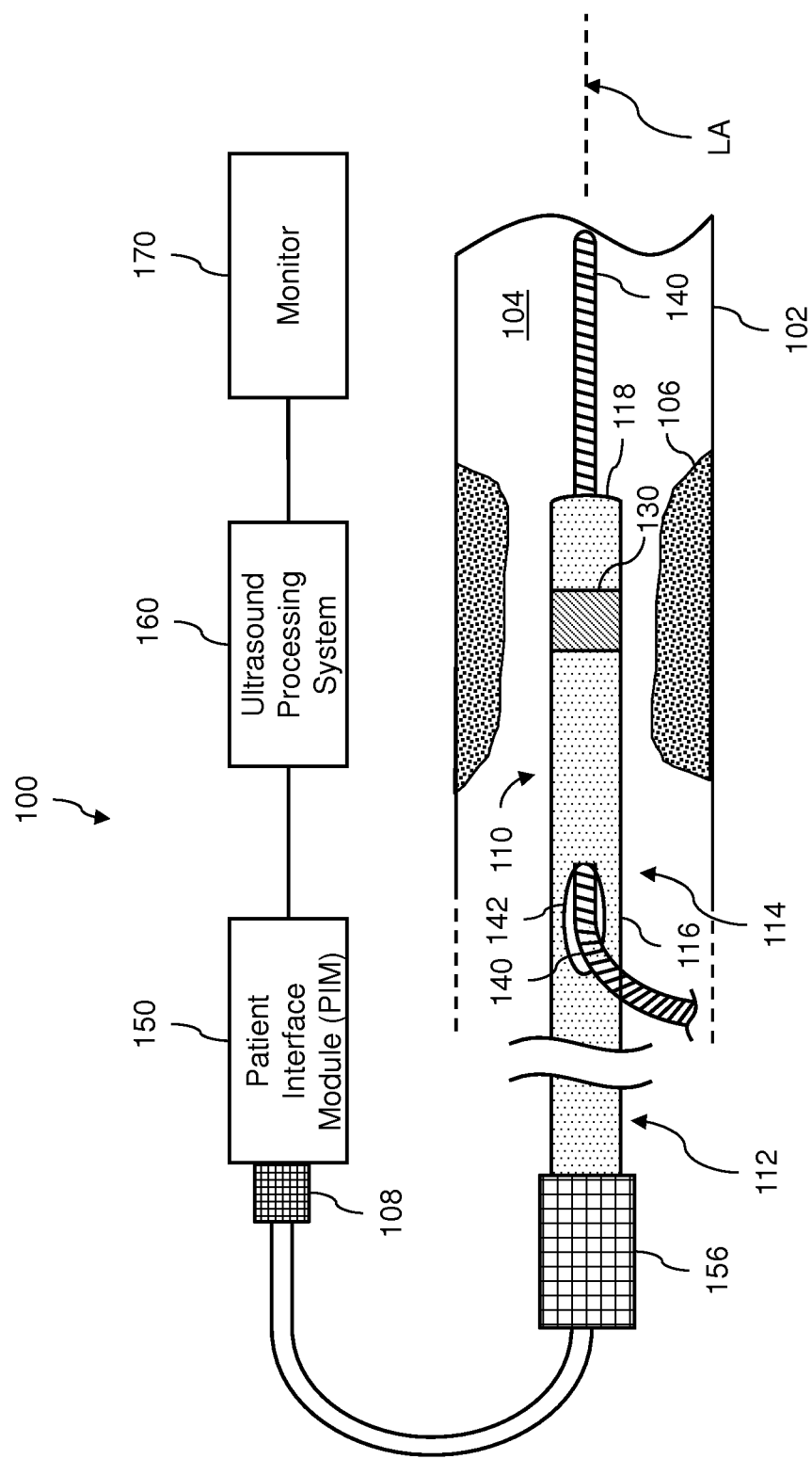
FIG. 1 is diagrammatic schematic view of an intraluminal ultrasound imaging system according to some embodiments of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an ultrasound system 100 according to some embodiments of the present disclosure. The ultrasound system 100 may be used to carry out intravascular ultrasound imaging of a lumen of a patient. The system 100 may include an ultrasound device 110, a patient interface module (PIM) 150, an ultrasound processing system 160, and/or a monitor 170. The ultrasound device 110 is structurally arranged (e.g., sized and/or shaped) to be positioned within anatomy 102 of a patient. The ultrasound device 110 obtains ultrasound imaging data from within the anatomy 102. The ultrasound processing system 160 can control the acquisition of ultrasound imaging and may be used to generate an image of the anatomy 102 (using the ultrasound imaging data received via the PIM 150) that is displayed on the monitor 170.

In some embodiments, the system 100 and/or the PIM 150 can include features similar to those described in U.S. Patent Application No. 62/574,455, titled "DIGITAL ROTATIONAL PATIENT INTERFACE MODULE," filed Oct. 19, 2017, U.S. Patent Application No. 62/574,687, titled "INTRALUMINAL DEVICE REUSE PREVENTION WITH PATIENT INTERFACE MODULE AND ASSOCIATED DEVICES, SYSTEMS, AND METHODS," filed Oct. 19, U.S. Patent Application No. 62/574,835, titled "INTRALUMINAL MEDICAL SYSTEM WITH OVERLOADED CONNECTORS," filed Oct. 20, 2017, and U.S. Patent Application No. 62/574,610, titled "HANDHELD MEDICAL INTERFACE FOR INTRALUMINAL DEVICE AND ASSOCIATED DEVICES, SYSTEMS, AND METHODS," filed Oct. 19, 2017, each of which is incorporated by reference in its entirety.

Generally, the ultrasound device 110 can be a catheter, a guide catheter, or a guide wire. The ultrasound device 110 includes a flexible elongate member 116. As used herein, "elongate member" or "flexible elongate member" includes at least any thin, long, flexible structure structurally arranged (e.g., sized and/or shaped) to be positioned within a lumen 104 of the anatomy 102. For example, a distal portion 114 of the flexible elongate member 116 is positioned within the lumen 104, while a proximal portion 112 of the flexible elongate member 116 is positioned outside of the body of the patient. The flexible elongate member 116 can include a longitudinal axis LA. In some instances, the longitudinal axis LA can be a central longitudinal axis of the flexible elongate member 116. In some embodiments, the flexible elongate member 116 can include one or more polymer/plastic layers formed of various grades of nylon, Pebax, polymer composites, polyimides, and/or Teflon. In some embodiments, the flexible elongate member 116 can include one or more layers of braided metallic and/or polymer strands. The braided layer(s) can be tightly or loosely braided in any suitable configuration, including any suitable per in count (pic). In some embodiments, the flexible elongate member 116 can include one or more metallic and/or polymer coils. All or a portion of the flexible elongate member 116 may have any suitable geometric cross-sectional profile (e.g., circular, oval, rectangular, square, elliptical, etc.) or non-geometric cross-sectional profile. For example, the flexible elongate member 116 can have a generally cylindrical profile with a circular cross-sectional profile that defines an outer diameter of the flexible elongate member 116. For example, the outer diameter of the flexible elongate member 116 can be any suitable value for positioning within the anatomy 102, including between approximately 1 Fr (0.33 mm) and approximately 15 Fr (5 mm), including values such as 3.5 Fr (1.17 mm), 5 Fr (1.67 mm), 7 Fr (2.33 mm), 8.2 Fr (2.73 mm), 9 Fr (3 mm), and/or other suitable values both larger and smaller.

The ultrasound device 110 may or may not include one or more lumens extending along all or a portion of the length of the flexible elongate member 116. The lumen of the ultrasound device 110 can be structurally arranged (e.g., sized and/or shaped) to receive and/or guide one or more other diagnostic and/or therapeutic instruments. If the ultrasound device 110 includes lumen(s), the lumen(s) may be centered or offset with respect to the cross-sectional profile of the device 110. In the illustrated embodiment, the ultrasound device 110 is a catheter and includes a lumen at the distal portion 114 of the flexible elongate member 116. A guide wire 140 extends through the lumen of the ultrasound device 110 between an entry/exit port 142 and an exit/entry port at a distal end 118 of the flexible elongate member 116. Generally, the guide wire 140 is a thin, long, flexible structure that is structurally arranged (e.g., sized and/or shaped) to be disposed within the lumen 104 of the anatomy 102. During a diagnostic and/or therapeutic procedure, a medical professional typically first inserts the guide wire 140 into the lumen 104 of the anatomy 102 and moves the guide wire 140 to a desired location within the anatomy 102, such as adjacent to an occlusion 106. The guide wire 140 facilitates introduction and positioning of one or more other diagnostic and/or therapeutic instruments, including the ultrasound device 110, at the desired location within the anatomy 102. For example, the ultrasound device 110 moves through the lumen 104 of the anatomy 102 along the guide wire 140. In some embodiments, the lumen of the ultrasound device 110 can extend along the entire length of the flexible elongate member 116. In the illustrated embodiment, the exit/entry port 142 is positioned proximally of components 130 of the ultrasound device 110. In some embodiments, the exit/entry port 142, the exit/entry port at the distal end 118, and/or the lumen of the ultrasound device 110 is positioned distally of the components 130. In some embodiments, the ultrasound device 110 is not used with a guide wire, and the exit/entry port 142 can be omitted from the ultrasound device 110.

The anatomy 102 may represent any fluid-filled or surrounded structures, both natural and man-made. For example, the anatomy 102 can be within the body of a patient. Fluid can flow through the lumen 104 of the anatomy 102. In some instances, the ultrasound device 110 can be referenced as an intraluminal device. The anatomy 102 can be a vessel, such as a blood vessel, in which blood flows through the lumen 104. In some instances, the ultrasound device 110 can be referenced as an intravascular device. In various embodiments, the blood vessel is an artery or a vein of a patient's vascular system, including cardiac vasculature, peripheral vasculature, neural vasculature, renal vasculature, and/or any other suitable anatomy/lumen inside the body. The anatomy 102 can be tortuous in some instances. For example, the device 110 may be used to examine any number of anatomical locations and tissue types, including without limitation, organs including the liver, heart, kidneys, gall bladder, pancreas, lungs, esophagus; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 110 may be used to examine man-made structures such as, but without limitation, heart valves, stents, shunts, filters and other devices.

The occlusion 106 of the anatomy 102 is generally representative of any blockage or other structural arrangement that results in a restriction to the flow of fluid through the lumen 104, for example, in a manner that is deleterious to the health of the patient. For example, the occlusion 106 narrows the lumen 104 such that the cross-sectional area of the lumen 104 and/or the available space for fluid to flow through the lumen 104 is decreased. Where the anatomy 102 is a blood vessel, the occlusion 106 may be a result of plaque buildup, including without limitation plaque components such as fibrous, fibro-lipidic (fibro fatty), necrotic core, calcified (dense calcium), blood, fresh thrombus, and/or mature thrombus. In some instances, the occlusion 106 can be referenced as thrombus, a stenosis, and/or a lesion. Generally, the composition of the occlusion 106 will depend on the type of anatomy being evaluated. Healthier portions of the anatomy 102 may have a uniform or symmetrical profile (e.g., a cylindrical profile with a circular cross-sectional profile). The occlusion 106 may not have a uniform or symmetrical profile. Accordingly, diseased portions of the anatomy 102, with the occlusion 106, will have a non-symmetric and/or otherwise irregular profile. While the anatomy 102 is illustrated in FIG. 1 as having a single occlusion 106, it is understood that the devices, systems, and methods described herein have similar application for anatomy having multiple occlusions.

The ultrasound device 110 may include ultrasound imaging components 130 disposed at the distal portion 114 of the flexible elongate member 116. The ultrasound imaging components 130 may be configured to emit ultrasonic energy into the anatomy 102 while the device 110 is positioned within the lumen 104. In some embodiments, the components 130 may include various numbers and configurations. For example, some of the components 130 may be configured to transmit ultrasound pulses while other others may be configured to receive ultrasound echoes. The components 130 may be configured to emit different frequencies of ultrasonic energy into the anatomy 102 depending on the type of tissue being imaged and the type of imaging being used.

In some embodiments, the components 130 include ultrasound transducer(s). For example, the components 130 can be configured to generate and emit ultrasound energy into the anatomy 102 in response to being activated by an electrical signal. In some embodiments, the components 130 include a single ultrasound transducer. In some embodiments, the components 130 include an ultrasound transducer array including more than one ultrasound transducer. For example, an ultrasound transducer array can include any suitable number of individual transducers between 2 transducers and 1000 transducers, including values such as 2 transducers, 4 transducers, 36 transducers, 64 transducers, 128 transducers, 500 transducers, 812 transducers, and/or other values both larger and smaller. The ultrasound transducer array including components 130 can be any suitable configuration, such as phased array including a planar array, a curved array, a circumferential array, an annular array, etc. For example, the ultrasound transducer array including components 130 can be a one-dimensional array or a two-dimensional array in some instances.

In some instances, the ultrasound imaging components 130 may be part of a rotational ultrasound device as described in U.S. Patent Application No. 62/574,455, titled "DIGITAL ROTATIONAL PATIENT INTERFACE MODULE," filed Oct. 19, 2017.

In some embodiments, the active area of the ultrasound imaging components 130 can include one or more transducer materials and/or one or more segments of ultrasound elements (e.g., one or more rows, one or more columns, and/or one or more orientations) that can be uniformly or independently controlled and activated. The active area of the components 130 can be patterned or structured in various basic or complex geometries. The components 130 can be disposed in a side-looking orientation (e.g., ultrasonic energy emitted perpendicular and/or orthogonal to the longitudinal axis LA) and/or a forward-looking looking orientation (e.g., ultrasonic energy emitted parallel to and/or along the longitudinal axis LA). In some instances, the components 130 are structurally arranged to emit and/or receive ultrasonic energy at an oblique angle relative to the longitudinal axis LA, in a proximal or distal direction. In some embodiments, ultrasonic energy emission can be electronically steered by selective triggering of ultrasound imaging components 130 in an array.

The ultrasound transducer(s) of the components 130 can be a piezoelectric micromachined ultrasound transducer (PMUT), capacitive micromachined ultrasonic transducer (CMUT), single crystal, lead zirconate titanate (PZT), PZT composite, other suitable transducer type, and/or combinations thereof. Depending on the transducer material, the manufacturing process for ultrasound transducer(s) can include dicing, kerfing, grinding, sputtering, wafer technologies (e.g., SMA, sacrificial layer deposition), other suitable processes, and/or combinations thereof.

In some embodiments, the components 130 are configured to obtain ultrasound imaging data associated with the anatomy 102, such as the occlusion 106. The ultrasound imaging data obtained by the ultrasound imaging components 130 can be used by a medical professional to diagnose the patient, including evaluating the occlusion 106 of the anatomy 102. For imaging, the components 130 can be configured to both emit ultrasonic energy into the lumen 104 and/or the anatomy 102, and to receive reflected ultrasound echoes representative of fluid and/or tissue of lumen 104 and/or the anatomy 102. As described herein, components 130 can include an ultrasound imaging element, such as an ultrasound transducer and/or an ultrasound transducer array. For example, the components 130 generate and emit ultrasound energy into the anatomy 102 in response to transmission of an electrical signal to the components 130. For imaging, the components 130 may generate and transmit an electrical signal representative of the received reflected ultrasound echoes from the anatomy 102 (e.g., to the PIM 150 and/or processing system 160). Based on the IVUS imaging data obtained by the ultrasound imaging components 130, the IVUS imaging system 160 assembles a two-dimensional image of the vessel cross-section from a sequence of several hundred of these ultrasound pulse/echo acquisition sequences occurring during a single revolution of the ultrasound imaging components 130.

In various embodiments, the ultrasound imaging component 130 can obtain imaging data associated with intravascular ultrasound (IVUS) imaging, forward looking intravascular ultrasound (FL-IVUS) imaging, intravascular photoacoustic (IVPA) imaging, intracardiac echocardiography (ICE), transesophageal echocardiography (TEE), and/or other suitable imaging modalities. In some embodiments, the device 110 can include an imaging component of any suitable imaging modality, such as optical imaging, optical coherence tomography (OCT), etc. In some embodiments, the device 110 can include any suitable sensing component, including a pressure sensor, a flow sensor, a temperature sensor, an optical fiber, a reflector, a mirror, a prism, an ablation element, a radio frequency (RF) electrode, a conductor, and/or combinations thereof. The imaging and/or sensing components can be implemented in the device 110 in lieu of or in addition to the ultrasound component 130.

For diagnosis and/or imaging, the center frequency of the components 130 can be between 2 MHz and 75 MHz, for example, including values such as 2 MHz, 5 MHz, 10 MHz, 20 MHz, 40 MHz, 45 MHz, 60 MHz, 70 MHz, 75 MHz, and/or other suitable values both larger and smaller. For example, lower frequencies (e.g., between 2 MHz and 10 MHz) can advantageously penetrate further into the anatomy 102, such that more of the anatomy 102 is visible in the ultrasound images. Higher frequencies (e.g., 50 MHz, 75 MHz) can be better suited to generate more detailed ultrasound images of the anatomy 102 and/or fluid within the lumen 104. In some embodiments, the frequency of the ultrasound imaging components 130 is tunable. For imaging, in some instances, the components 130 can be tuned to receive wavelengths associated with the center frequency and/or one or more harmonics of the center frequency. In some instances, the frequency of the emitted ultrasonic energy can be modified by the voltage of the applied electrical signal and/or the application of a biasing voltage to the ultrasound imaging components 130.

In some embodiments, the ultrasound imaging components 130 are positioned at the distal portion of the flexible elongate member 116. The ultrasound imaging components 130 can include one or more electrical conductors extending along the length from the flexible elongate member 116. The electrical conductor(s) are in communication with the ultrasound imaging components 130 at the distal portion 114, and an interface 156 at the proximal portion 112. The electrical conductors carry electrical signals between the ultrasound processing system 160 and the ultrasound imaging components 130. For example, activation and/or control signals can be transmitted from the processing system 160 to the ultrasound imaging components 130 via the electrical conductors. Electrical signals representative of the reflected ultrasound echoes can be transmitted from the ultrasound imaging components 130 to the processing system 160 via the electrical conductors. In some embodiments, the same electrical conductors can be used for communication between the processing system 160 and the ultrasound imaging components 130.

The ultrasound device 110 includes an interface 156 at the proximal portion 112 of the flexible elongate member 116. In some embodiments, the interface 156 can include a handle. For example, handle can include one or more actuation mechanisms to control movement of the device 110, such as deflection of the distal portion 114. In some embodiments, the interface 156 can include a telescoping mechanism that allows for pullback of the device 110 through the lumen. In some embodiments, the interface 156 can include a rotation mechanism to rotate one or more components of the device 110 (e.g., the flexible elongate member 116 and the ultrasound imaging components 130). In some embodiments, the interface 156 includes a user interface component (e.g., one or more buttons, a switch, etc.) for a medical professional to selectively activate the ultrasound imaging components 130. In other embodiments, a user interface component of the PIM 150, the processing system 160 and/or the monitor 170 allows a medical profession to selectively activate the ultrasound imaging components 130. A conduit including, e.g., electrical conductors, extends between the interface 156 and the connector 108. The connector 108 can be configured to mechanically and/or electrically couple the device 110 to the PIM 150.

The ultrasound processing system 160, the PIM 150, and/or the intravascular ultrasound device 110 (e.g., the interface 156, the ultrasound imaging components 130, etc.) can include one or more controllers. The controllers can be integrated circuits, such as application specific integrated circuits (ASIC), in some embodiments. The controllers can be configured to select the particular transducer element(s) to be used for transmit and/or receive, to provide the transmit trigger signals to activate the transmitter circuitry to generate an electrical pulse to excite the selected transducer element(s), and/or to accept amplified echo signals received from the selected transducer element(s) via amplifiers of controllers. Multiple ASIC configurations with various numbers of master circuits and slave circuits can be used to create a single ultrasound wave or multi-firing ultrasound wave device.

In some embodiments, the PIM 150 performs preliminary processing of the ultrasound echo data prior to relaying the data to the console or processing system 160. In examples of such embodiments, the PIM 150 performs amplification, filtering, and/or aggregating of the data. In an embodiment, the PIM 150 also supplies high- and low-voltage DC power to support operation of the device 110 including circuitry associated with the ultrasound transducers 130.

In some embodiments, the PIM 150 is powered by a wireless charging system. The wireless charging system may include an inductive charging system. For example, the PIM 150 may include a battery that is charged with a Qi inductive charging base. This may allow for a portable PIM 150. Furthermore, an internal battery of the PIM 150 may produce low enough current that electrical isolation components are not required. In other embodiments, the PIM 150 includes a charging cable in addition to the internal battery. In this case, the PIM 150 may be an isolation device as, in various surgical settings, patient safety requirements mandate physical and electrical isolation of the patient from one or more high voltage components.

The ultrasound processing system 160 receives imaging data (e.g., electrical signals representative of the ultrasound echo data) from the ultrasound imaging components 130 by way of the PIM 150. The processing system 160 can include processing circuit, such as processor and/or memory. The ultrasound processing system 160 processes the data to reconstruct an image of the anatomy. The processing system 160 outputs image data such that an image of the anatomy 102, such as a cross-sectional IVUS image of a vessel, is displayed on the monitor 170. The processing system 160 and/or the monitor 170 can include one or more user interface elements (e.g., touchscreen, keyboard, mouse, virtual buttons on a graphical user interface, physical buttons, etc.) to allow a medical professional to control the device 110, including one or more parameters of the ultrasound imaging components 130.

In some embodiments, imaging data is transmitted from the PIM 150 to the ultrasound processing system 160 wirelessly. For example, the PIM 150 may be configured to transmit imaging data with a wireless Ethernet protocol. The PIM 150 and ultrasound processing system 160 may include a wireless transmitter and receiver, such as a wireless router. In some embodiments the wireless router is included in the ultrasound processing system 160 and not the PIM 150. The PIM 150 may also include a function to cease all transmissions, wired and wireless, when the PIM 150 is charging.

Figure 2:
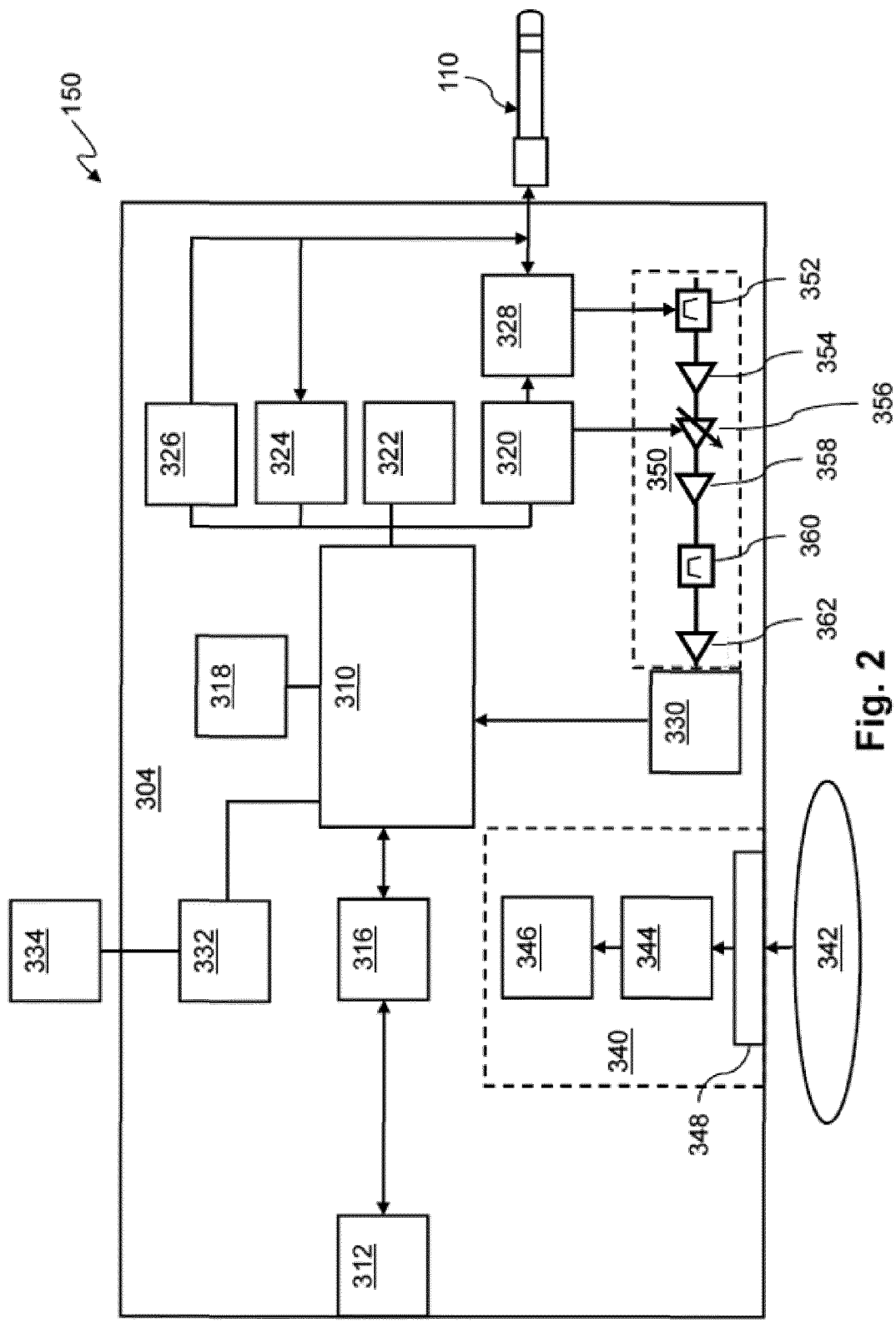
FIG. 2 is diagrammatic perspective view of a patient interface module (PIM) according to some embodiments of the present disclosure.

FIG. 2 is a diagrammatic schematic view of a PIM 150. In some embodiments, the PIM 150 is communicatively disposed between the ultrasound device 110 and the processing system 160. The PIM 150 may be used to transmit commands and signals to the ultrasound device 110, as well as to receive, process, and transmit ultrasound echo signals from the ultrasound device 110. In some embodiments, these ultrasound echo signals are transmitted along a differential signal path in the PIM 150, and are digitized and formatted for Ethernet transmission to the ultrasound processing system 160.

The PIM 150 may include an outer housing 304. The housing 304 may be suitable for use in a sterile environment (i.e., water resistant) and may be sized to be suitable for use on an operating table. In some embodiments, the housing 304 includes internal sections to house various components. For example, the housing 304 may include particular housing sections to contain the power system 340, the signal chain 350, and the controller 310 and associated components.

The controller 310 of the PIM 150 may be configured to transmit signals to other elements of the PIM 150 as well as to external devices, such as the ultrasound device 110, processing system 160, and monitor 170. In some embodiments, the controller 310 is a field-programmable gate array (FPGA). In other embodiments, the controller 310 is a central processing unit (CPU), a digital signal processor (DSP), an application-specific integrated circuit (ASIC), another hardware device, a firmware device, or any combination thereof configured to perform the operations described herein with reference to the controller 310 as shown in FIG. 2 above.

The controller 310 may be connected to a memory 318. In some embodiments, the memory is a random access memory (RAM). In other embodiments, the memory 318 is a cache memory (e.g., a cache memory of the controller 310), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In some embodiments, the memory 318 may include a non-transitory computer-readable medium. The memory 318 may store instructions. The instructions may include instructions that, when executed by a processor, cause the processor to perform operations described herein with reference to the controller 310 in connection with embodiments of the present disclosure.

The controller 310 may be connected to a catheter motor 326, EEPROM 324, transmitter 322, and a time gain compensation (TGC) control 320. In some embodiments, the catheter motor 326 is configured to move the ultrasound device 110 within a lumen. The catheter motor 326 may include a rotational component for rotating a portion of the ultrasound device 110. The catheter motor 326 may also include a motor for moving the ultrasound device 110 along lumens within the body of the patient.

The transmitter 322 may be any type of transmission device for sending signals to the ultrasound device 110. In some embodiments, the controller 310 is configured to control the ultrasound device 110 by sending signals through the transmitter 322. In this way, the controller 310 may be configured to drive the transmission of ultrasound signals by the ultrasound device 110. The direction of transmission and signal strength of the ultrasound signals may be controlled by the controller 310. The transmitter 322 may be connected to a transmit/receive (T/R) switch 328. In some embodiments, the T/R switch 328 may be configured to change between transmit and receive modes. For example, the controller 310 may send a signal to the ultrasound device 110 while the T/R switch 328 is in transmit mode. Data (such as ultrasound echo signals) may be transmitted back from the ultrasound device 110 to the PIM 150. This data may be stored by the EEPROM 324. When the ultrasound echo signals are transmitted back from the ultrasound device 110 to the PIM 150, the T/R switch 328 may be set to receive mode to receive and direct the ultrasound echo signals along the correct signal route.

The ultrasound echo signals may be received by the PIM 150 and directed along a differential signal route. In some embodiments, the differential signal route may include a signal chain 350 including one or more elements 352, 354, 356, 358, 360, 362. The differential signal route may help to cancel common mode noise, and in particular "white noise/flicker" which can occur in existing image processing systems. The differential signal route and associated signal chain 350 may result in a more noise free signal and improved image quality. The signal chain 350 may provide filtering and programmable gain functions. In some embodiments, the TGC control 320 is a time varying gain that adjusts for signal loss as the distance between the PIM 150 and the ultrasound device 110 increases. The gain is typically reduced for near reflections and gradually increased for distant reflections. The amount of gain over distance may be controlled, for example by the controller 310 of the PIM 150. In some embodiments, the TGC control may be configured to control the signal amplification of the received ultrasound echo signals. The TGC control 320 may also be configured to set the receive path for the ultrasound echo signals along the signal chain 350. The signal chain 350 may include bandpass filters 352, 360 and amplifiers 354, 356, 358, 362. For example, the ultrasound echo signals from the ultrasound device 110 may be passed in order through a first bandpass filter 352, a first fixed amplifier 354, a variable gain amplifier 356, a first buffer amplifier 358, a second bandpass filter 360, and a second buffer amplifier 362. In some embodiments, the bandpass filters 352, 360 allow signals between 20 and 40 MHz. In other embodiments, the bandpass filters allow other ranges of signals, such as 10 to 50 MHz, 5 to 60 MHz, and other ranges.

After the signals are passed through the signal chain 350, they may be transmitted to an analog to digital converter (ADC) 330. The ADC 330 may digitize the ultrasound echo signals for processing by the controller 310. The signals may then be prepared for transmission to the ultrasound processing system 160. In some embodiments, the signals from the ultrasound device 110 may be transmitted by a wireless connection to the ultrasound processing system 160. For example, the signals may be transmitted by a wireless transmitter 312. The wireless transmitter 312 may be any type of transmitter that is configured to send wireless signals. The wireless transmitter 312 may include an antennae disposed on an outer surface of the housing 304 or within the housing 304. Generally, the wireless transmitter 312 may be configured to use any current or future developed wireless protocol(s). For example, the wireless transmitter may be configured for wireless protocols including WiFi, Bluetooth, LTE, Z-wave, Zigbee, WirelessHD, WiGig, etc. In some embodiments, the wireless transmitter 312 is configured to transmit wireless Ethernet signals. In this case, the signals from the ultrasound device 110 (which have been digitized by the ADC 330) are transmitted to an Ethernet physical layer (PHY) 316. The Ethernet PHY may be configured to convert the signals from the ultrasound device 110 for an Ethernet connection. The converted signals may then be passed to a wireless transmitter 312 and transmitted to the ultrasound processing system 160. In some embodiments, the wireless transmitter 312 also includes a wired Ethernet connection. In this case, the wireless transmitter 312 may include one or more Ethernet cables as well as associated ports.

In other embodiments, the PIM 150 may be configured to transmit data from the ultrasound device 110 to the ultrasound processing system 160 via other protocols, such as USB (and in particular, USB 3.0). In this case, the PIM 150 may include a wireless USB transmitter the signals from the ultrasound device 110 may be configured for use with USB.

The PIM 150 may include a pullback motor 332 which may be used to pull the ultrasound device 110 through a lumen to collect imaging data. The pullback motor 332 may be configured to pull the ultrasound device 110 at a constant speed. The pullback motor 332 may be connected to an external pullback sled 334.

The PIM 150 may include a wireless power system 340. In some embodiments, this wireless power system may include an inductive charging system. The inductive charging system may include an inductive coupling system, such as a Qi inductive charging system. This power system 340 may include an inductive charging base 342, a battery 344 within the PIM 150, and a power distributor 346 that is configured to provide power to the various components of the PIM 150. In some embodiments, the inductive charging base 342 is wireless and the battery 344 is rechargeable. The PIM 150 may be placed on the inductive charging base 342 to recharge its battery 344. Due to the separation between the PIM 150 and the inductive charging base 342, isolation components may not be required within the PIM 150, for example, if the PIM 150 has a minimum creepage distance of 4 mm of isolation from the ultrasound device 110 or the inductive charging base 342. In other embodiments, the minimum creepage distance may be 2 mm, 6 mm, 8 mm, or other distances. In other embodiments, the wireless power system is a resonant inductive coupling system, a capacitive coupling system, or a magnetodynamic coupling system. In some embodiments, the PIM 150 is configured to receive power from microwaves, lasers, and/or light waves.

In some embodiments, the PIM 150 is configured to stop all transmissions while it is connected to the charging base 342. This may help to prevent high levels of current to be passed between the PIM 150 and other components (such as the ultrasound device 110) which could cause harm to a patient. This function to stop transmissions during charging may reduce the number of isolation components that are required within the PIM 150. In some embodiments, this function is provided by a connector 348 of the PIM 150. The connector 348 may be disposed on an external portion of the housing 304, and may be configured to stop transmissions from the PIM 150 while the PIM 150 is connected to the charging base 342. The connector 348 may include mechanical features such as pins, flanges, projections, extensions, or other devices to effectively couple the PIM 150 to the inductive charging base 342 and provide a signal to the PIM 150 that it is connected. In some embodiments, the connector 348 includes a switch 349, similar to FIG. 3, that has "on" and "off" modes. The switch 349 may be connected to the controller 310 of the PIM 150. When the PIM 150 is connected to the charging base 342, the switch 349 may be in the "off" mode which may prevent the PIM 150 from transmitting signals to other devices, such as the ultrasound device 110. When the PIM 150 is disconnected from the charging base 342, the switch 349 may be in the "on" mode, allowing transmissions from the PIM 150 to other devices.

In some embodiments, the PIM 150 is powered by power over Ethernet (PoE). In this case, power may be input through the transmitter 312 or through another Ethernet connection on the PIM 150. The power may then be distributed throughout the PIM 150 by the power distributor 346.

Figure 3:
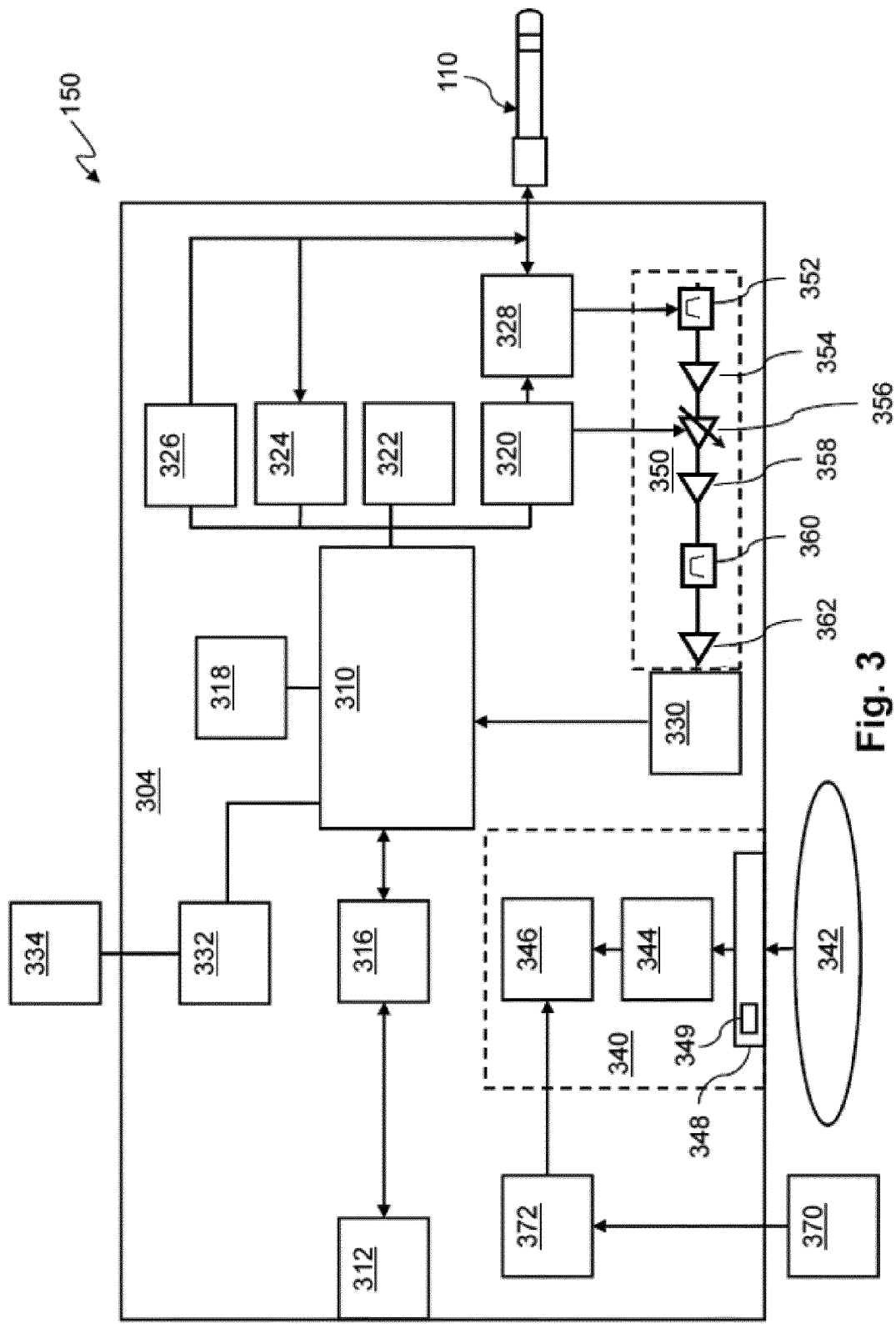
FIG. 3 is diagrammatic perspective view of a PIM with a charging cable according to some embodiments of the present disclosure.

FIG. 3 is a diagrammatic schematic view of a PIM 150 that may be connected to charging cable 370. In this case, the PIM 150 may be powered by the charging cable 370 or the power system 340 including the inductive charging base 342. The charging cable 370 may be a Power over Ethernet (PoE) device or another type of power device, such as a custom power cable. The charging cable 370 may be connected to the power distributor 346. An isolation device 372 may be disposed between the charging cable 370 and the power distributor 346.

In some embodiments, power is only passed through the isolation device 372 when the PIM 150 is connected to the charging cable 370. This may allow a user to choose between using the PIM 150 in a wireless, battery-powered mode or a wired, cable-charged mode while still protecting the patient from high current levels. Since this embodiment includes an isolation device 372 along the wired power input, the PIM 150 may be configured to transmit and receive signals even while the PIM 150 is connected to the charging cable 370.

Figure 4:
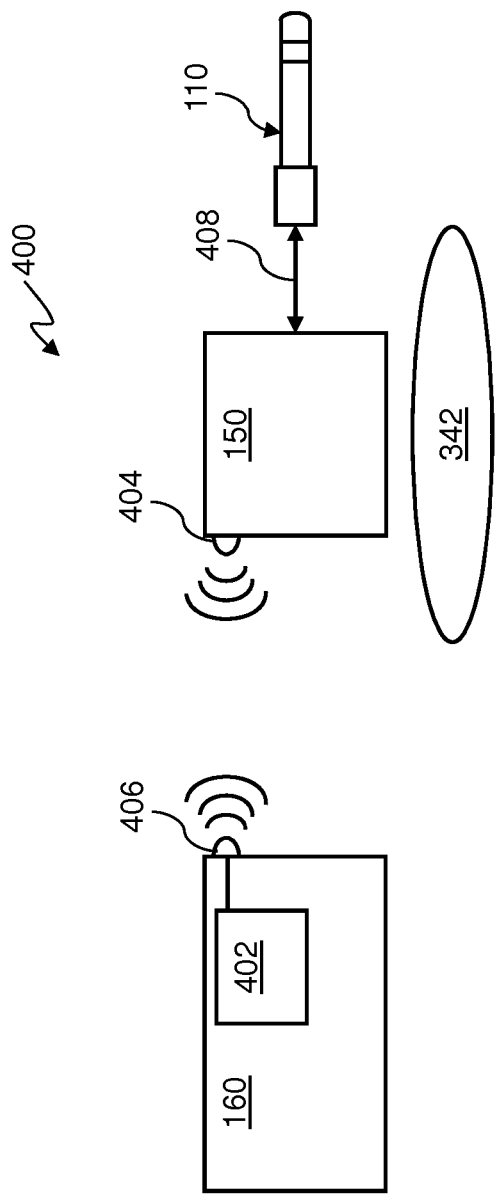
FIG. 4 is diagrammatic schematic view of a PIM transmitting signals to a processing system according to some embodiments of the present disclosure.

FIG. 4 is diagrammatic schematic view 400 of a PIM 150 transmitting signals to an ultrasound processing system 160. In some embodiments, the PIM 150 includes a wireless transmitter 404 and the ultrasound processing system 160 includes a wireless receiver 406. In some embodiments, the wireless receiver 404 is connected to a wireless router 402. In the example of FIG. 4, imaging data (such as ultrasound echo signals) are transmitted through a cable 408 from an ultrasound device 110 positioned within a lumen of the patient to the PIM 150. This imaging data may be digitized and processed by the PIM 150. The digitized data may then be wirelessly transmitted from the PIM 150 to the ultrasound processing system 160. In this case, the PIM 150 may be powered by a battery such that the PIM 150 is portable. As discussed above, the battery within the PIM 150 may be chargeable via an inductive charging base 342. However, during the transmission and reception of signals, the PIM 150 may not be connected to the inductive charging base 342.

Figure 5:
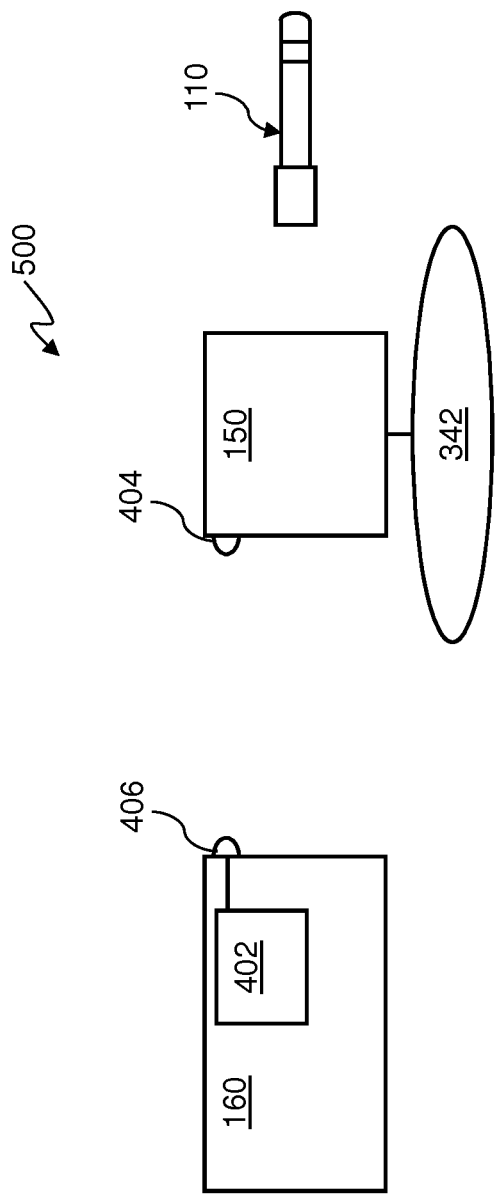
FIG. 5 is diagrammatic schematic view of a PIM charging on a wireless charger according to some embodiments of the present disclosure.

FIG. 5 is diagrammatic schematic view 500 of a PIM 150 that is connected to an inductive charging base 342. In this example, the PIM 150 may not transmit or receive signals from other devices such as the ultrasound device 110 or the ultrasound processing system 160. As shown in FIG. 5, the PIM 150 is not connected to the ultrasound device 110 and is not transmitting to the ultrasound processing system 160. In other embodiments, when the PIM 150 is connected to the inductive charging base 342, wireless transmission of signals may continue while wired transmission is stopped. For example, while the PIM 150 is connected to the charging base 342 the PIM 150 may transmit wireless to the ultrasound processing system 160 but not transmit or receive signals from the ultrasound device 110.

Figure 6:
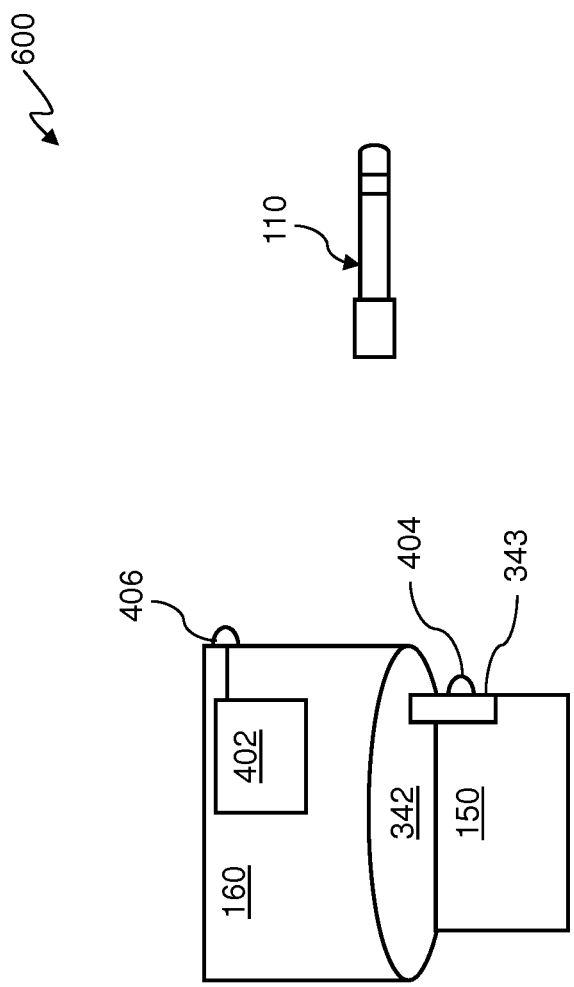
FIG. 6 is diagrammatic schematic view of a PIM charging on a wireless charger on a processing system according to some embodiments of the present disclosure.

FIG. 6 is diagrammatic schematic view 600 of a processing system 160 that includes an integrated inductive charging base 342. The PIM 150 may be placed on this inductive charging base 342 (and connected to the processing system 160) to charge. The inductive charging base 342 may include a device 343 that prevents the PIM 150 from being connected to the ultrasound device 110 when connected. The device 343 may be any type of mechanical or electrical device for preventing connection between the PIM 150 and the ultrasound device 110. For example, the device 343 may automatically turn a switch preventing connection (as discussed in FIG. 3) or the device 343 may physically plug or otherwise disable a connector on the PIM 150 such that the ultrasound device 110 may not be connected to the PIM 150 when the device 343 is activated. The device 343 may also electrically disable the transmission and reception of signals to and from the PIM 150 while the PIM 150 is connected to the inductive charging base 342.

Figure 7:
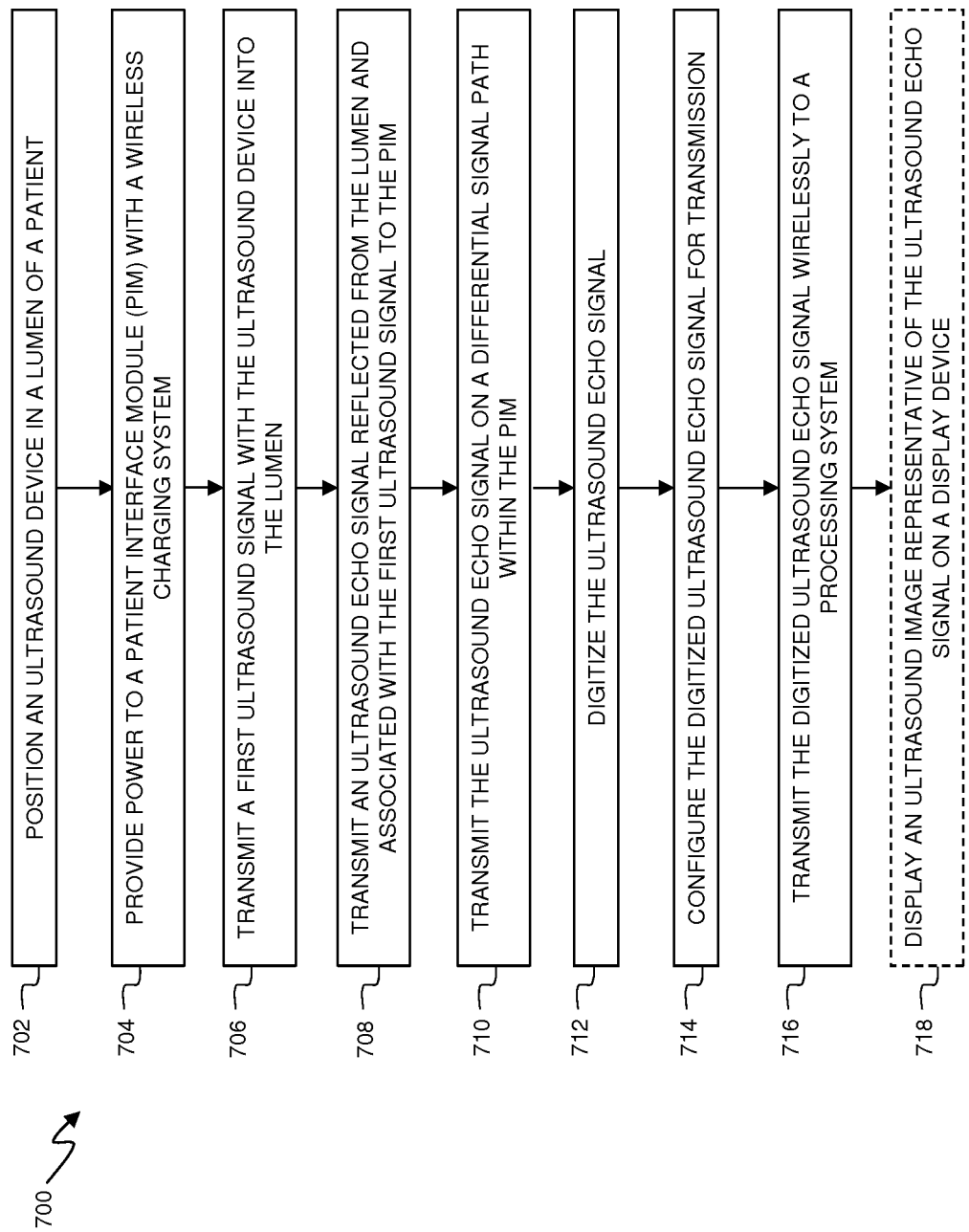
FIG. 7 is a flow diagram of an ultrasound imaging method according to embodiments of the present disclosure.

FIG. 7 provides a flow diagram illustrating a method 700 of intravascular ultrasound imaging. As illustrated, the method 700 includes a number of enumerated steps, but embodiments of the method 700 may include additional steps before, after, and in between the enumerated steps. In some embodiments, one or more of the enumerated steps may be omitted, performed in a different order, or performed concurrently. The method 700 may be performed using any of the systems and devices referred to in FIGS. 1-6.

At step 702, the method 700 may include positioning an ultrasound device in a body lumen of a patient. The ultrasound device may be similar to the ultrasound device 110 as shown in FIGS. 1-6. In particular, the ultrasound device may be an intravascular rotational ultrasound device with one or more imaging ultrasound transducer elements at the distal portion of a rotating drive cable. The step 702 can include placing a sheath and the imaging core/drive cable within the lumen of the anatomy. The drive cable can be disposed within the sheath of the ultrasound device.

At step 704, the method 700 may include providing power to a patient interface module (PIM) with a wireless charging system, such as a power system 340 as shown in FIGS. 2 and 3. The PIM may be connected to the ultrasound device and configured to transmit signals to and receive signals from the ultrasound device when the PIM is not charging. In some embodiments, the wireless charging system includes an inductive charging base (such as a Qi inductive charging base) and a battery within the PIM. The wireless charging system may include one or more devices to prevent connection of the PIM to other devices while charging, such as the ultrasound device.

At step 706, the method 700 may include transmitting a first ultrasound signal with the ultrasound device into the lumen. The first ultrasound signal may be transmitted with one or more ultrasound elements of the ultrasound device. In some embodiments, the transmission of the first ultrasound signal may be controlled by a patient interface module (PIM) such as PIM 150 as shown in FIGS. 1-6. For example, a controller of the PIM may be used to send a signal to the ultrasound device, which may in turn be transmitted into the lumen by the one or more ultrasound elements of the ultrasound device. Step 704 may be performed while the drive cable of the ultrasound device and the one or more ultrasound elements are rotating within the sheath positioned inside the lumen. In that regard, the method 700 can include connecting the ultrasound device and/or the drive cable to a movement device, such as a pullback device, that is configured to rotate and/or longitudinally translate the ultrasound device. The first ultrasound signal may be reflected off anatomy (e.g., tissue, blood vessel, plaque, etc.) within the lumen in the form of ultrasound echoes, some of which may travel back toward the first ultrasound element. These ultrasound echo signals may be received by the ultrasound device, such as with one or more transducer elements.

At step 708, an ultrasound echo signal associated with the first ultrasound signal may be transmitted to the PIM. In some embodiments, the ultrasound echo signal is received by a transmit/receive (T/R) switch, such as T/R switch 328 as shown in FIGS. 2 and 3. The ultrasound echo signal may be processed by the PIM in preparation for its use in creating ultrasound images of the lumen.

At step 710, the ultrasound echo signal may be transmitted on a differential signal path within the PIM. In some embodiments, the differential signal path may help to reduce noise. The differential signal path may include a signal chain with one or more amplifiers and buffers. In some embodiments, the differential signal path includes, in order, a first bandpass filter, a first fixed amplifier, a variable gain amplifier, a first buffer amplifier, a second bandpass filter, and a second buffer amplifier. In other embodiments, the differential signal path includes other combinations of elements.

At step 712, the ultrasound echo signal may be digitized. In some embodiments, after passing along the differential signal path, the ultrasound echo signal is transmitted to an ADC within the PIM. The ADC may be used to digitize the ultrasound echo signal. The digitized ultrasound echo signal may then be transmitted to a controller within the PIM.

At step 714, the digitized ultrasound echo signal may be configured for transmission to another device, such as an ultrasound processing system. In some embodiments, this includes transmitting the digitized ultrasound echo signal to an Ethernet physical layer (PHY) with the controller of the PIM. Step 714 may also include passing the ultrasound echo signal to a wireless transmitter and configuring the digitized ultrasound echo signal for wireless transmission.

At step 716, the digitized ultrasound signal may be transmitted wirelessly to the processing system. The processing system may be the ultrasound processing system 160 as shown in FIG. 1. Step 716 may be carried out by using a wireless transmitter on the PIM and a wireless receiver on the processing system. The wireless signals transmitted may be wireless Ethernet signals. The processing system may be used to further process the digitized ultrasound echo signal to produce ultrasound images of the lumen of the patient.

At step 718, an ultrasound image representative of the ultrasound echo signal may optionally be displayed on a display device. The display device may be similar to the monitor 170 as shown in FIG. 1. For example, the image can be an IVUS image of a blood vessel.

Persons skilled in the art will recognize that the apparatus, systems, and methods described above can be modified in various ways. While in the present disclosure it is referred primarily to intraluminal ultrasound device, intraluminal ultrasound system and intraluminal ultrasound imaging method, the device may be any sensing device configured to provide measurements within the body (e.g. physiological measurements such as pressure, flow velocity, electric activation signals), a corresponding sensing system and sensing method. The sensing device substitutes the intraluminal ultrasound device in the system and method disclosed herein for those alternative embodiments. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

The invention claimed is:

1. A sensing system, comprising:
a patient interface module (PIM) communicatively disposed between a processing system and a sensing device configured to be positioned within a body of a patient, the PIM comprising a transmitter, an analog to digital converter (ADC), a communication device, and a power source,
wherein, in an operating mode, the power source is configured to power the PIM to transmit and receive signals associated with at least one of the sensing device or the processing system,
wherein, in a charging mode, the power source is configured to be recharged by a wireless charging system,
wherein, in the operating mode, the PIM is configured to:
transmit, with the transmitter, a first signal to the sensing device;
receive a measurement signal associated with the first signal from the sensing device such that the sensing device obtains the measurement signal from the body of the patient and the PIM is different than the sensing device;
digitize the measurement signal with the ADC; and
transmit the digitized measurement signal to the processing system wirelessly via the communication device,
wherein, in the charging mode, the PIM is prevented from transmitting or receiving the signals such that the sensing device and the processing system do not operate with the PIM while the PIM is in the charging mode,
wherein the sensing device is an intraluminal ultrasound device configured to be positioned within a body lumen of the patient, and
wherein the measurement signal is ultrasound echo signal.

2. The system of claim 1, wherein the processing system is configured to generate an intraluminal ultrasound image representative of the ultrasound echo signal and to display the intraluminal ultrasound image on a display device in communication with the processing system.

3. The system of claim 1, wherein the power source comprises a rechargeable battery disposed within the PIM and a Qi inductive charging base.

4. The system of claim 3, wherein the PIM does not transmit or receive the signals when connected to the Qi inductive charging base.

5. The system of claim 3, wherein the PIM comprises a switch that prevents receiving or sending the signals with the PIM when is connected to the Qi inductive charging base.

6. The system of claim 1, wherein the PIM is further configured to be selectively powered by a charging cable.

7. The system of claim 1, wherein the PIM further comprises a controller in communication with the transmitter, the ADC, and the communication device.

8. The system of claim 7, wherein the controller is a field-programmable gate array (FPGA).

9. The system of claim 1, wherein the intraluminal ultrasound device comprises:
a rotatable, flexible elongate drive cable comprising a proximal portion and a distal portion; and
an ultrasound element disposed at the distal portion of the drive cable and configured to obtain imaging data of the body lumen while rotating.

10. The system of claim 1, wherein the intraluminal ultrasound device is an intravascular ultrasound (IVUS) device configured to be positioned within a blood vessel.

11. The system of claim 1, wherein the ultrasound echo signal travels on a differential signal path to the ADC within the PIM.

12. The system of claim 11, wherein the differential signal path comprises one or more amplifiers and bandpass filters.

13. A sensing method, comprising:
providing a patient interface module (PIM) communicatively disposed between a sensing device and a processing system, wherein the PIM comprises a power source,
in an operating mode:
powering, using the power source, the PIM to transmit and receive signals associated with at least one of the sensing device or the processing system,
controlling, using a transmitter of the PIM, the sensing device by transmitting a first signal to the sensing device when positioned within a body of a patient;
receiving, with PIM, a measurement signal associated with the first signal from the sensing device such that the sensing device obtains the measurement signal from the body of the patient and the PIM is different than the sensing device;
digitizing the measurement signal with an analog to digital converter (ADC) in the PIM; and
transmitting the digitized measurement signal to the processing system via a wireless communication device; and
in a charging mode:
recharging the power source using a wireless charging system; and
preventing the PIM from transmitting or receiving the signals such that the sensing device and the processing system do not operate with the PIM while the PIM is in the charging mode,
wherein the sensing device is an intraluminal ultrasound device configured to be positioned within a body lumen of the patient, and
wherein the measurement signal is ultrasound echo signal.

14. The method of claim 13, further comprising displaying, with a display device in communication with the processing system, an intraluminal ultrasound image representative of the ultrasound echo signal.

15. The method of claim 14, further comprising formatting, by the PIM, the ultrasound echo signal according to an image display format of the display device.

16. The method of claim 13, wherein the power source comprises a rechargeable battery disposed within the PIM and a Qi inductive charging base.

17. The method of claim 16, further comprising preventing the transmission of the signals by the PIM when the PIM is connected to the Qi inductive charging base.

18. The method of claim 13, further comprising transmitting the ultrasound echo signals signal along a differential signal path to the ADC within the PIM.

19. The method of claim 13, wherein the intraluminal ultrasound device comprises:
a rotatable, flexible elongate drive cable comprising a proximal portion and a distal portion; and
an ultrasound element disposed at the distal portion of the drive cable and configured to obtain imaging data of the body lumen while rotating.

20. The method of claim 13, wherein the intraluminal ultrasound device is an intravascular ultrasound (IVUS) device configured to be positioned within a blood vessel.

* * * * *